United States Patent
Pavlovic et al.

(10) Patent No.: US 11,166,901 B2
(45) Date of Patent: Nov. 9, 2021

(54) PHOTOPOLYMERIZABLE COATING FOR NAILS

(71) Applicant: Coty Inc., New York, NY (US)

(72) Inventors: Elizabeta Pavlovic, Los Angeles, CA (US); Sunan Yuvavanich, Thousand Oaks, CA (US)

( * ) Notice: Subject to any disclaimer, the term of this patent is extended or adjusted under 35 U.S.C. 154(b) by 0 days.

(21) Appl. No.: 16/349,480

(22) PCT Filed: Dec. 15, 2017

(86) PCT No.: PCT/US2017/066801
§ 371 (c)(1),
(2) Date: May 13, 2019

(87) PCT Pub. No.: WO2018/118708
PCT Pub. Date: Jun. 28, 2018

(65) Prior Publication Data
US 2020/0188281 A1    Jun. 18, 2020

Related U.S. Application Data

(60) Provisional application No. 62/438,085, filed on Dec. 22, 2016.

(51) Int. Cl.
*A61K 8/81* (2006.01)
*A61K 8/44* (2006.01)
*A61K 8/73* (2006.01)
*A61Q 3/02* (2006.01)
*A61Q 3/04* (2006.01)

(52) U.S. Cl.
CPC .............. *A61K 8/8147* (2013.01); *A61K 8/44* (2013.01); *A61K 8/731* (2013.01); *A61Q 3/02* (2013.01); *A61Q 3/04* (2013.01)

(58) Field of Classification Search
CPC ...... A61K 8/81; A61K 8/8147; A61K 8/8152; A61K 8/8461; A61K 8/87; A61Q 3/00; A61Q 3/02
See application file for complete search history.

(56) References Cited

U.S. PATENT DOCUMENTS

| | | | |
|---|---|---|---|
| 2013/0090443 A1* | 4/2013 | Musa | A01N 25/24 526/263 |
| 2015/0005465 A1* | 1/2015 | Hood | C08F 220/18 526/271 |
| 2016/0220474 A1* | 8/2016 | Flint | A61K 8/35 |

FOREIGN PATENT DOCUMENTS

| | | |
|---|---|---|
| WO | WO-2011011304 A2 | 1/2011 |
| WO | WO-2013190465 A2 | 12/2013 |
| WO | WO-2014028020 A1 | 2/2014 |

OTHER PUBLICATIONS

"International Application Serial No. PCT/US2017/066801, International Search Report dated Mar. 12, 2018", 5 pgs.
"International Application Serial No. PCT/US2017/066801, Written Opinion dated Mar. 12, 2018", 7 pgs.

* cited by examiner

*Primary Examiner* — Micah Paul Young
(74) *Attorney, Agent, or Firm* — Victoria Friedman; Dennemeyer & Associates, LLC

(57) ABSTRACT

A photopolymerizable composition for forming a photopolymerized nail top coating of a substantially uniform mixture of ethyl cellulose and crosslinked (meth)acrylate polymer is disclosed.

20 Claims, No Drawings

PHOTOPOLYMERIZABLE COATING FOR NAILS

PRIORITY

This application is a U.S. National Stage Filing under 35 U.S.C. 371 from International Application No. PCT/US2017/066801, filed on Dec. 15, 2017, and published as WO 2018/118708 on Jun. 28, 2018, which claims the benefit of priority from U.S. Provisional Patent Application Ser. No. 62/438,085, filed on Dec. 22, 2016, which is herein incorporated by reference in its entirety.

BACKGROUND

Commercial gel nail coatings typically include a base coat, a color coat and a top coat. Recent developments in the technology combine pre-existing film forming polymers such as cellulose acetate butyrate with photopolymerizable gels based upon (meth)acrylate technology. The gels include crosslinkers that contribute hardness, resistance to dissolution, resistance to scratching and long wear yet in combination with film formers contribute flexibility. Nail salons are the typical commercial establishments handling this work because it entails careful application and curing by UV radiation.

Photopolymerizable (meth)acrylate coatings find significant applications in diverse commercial fields including not only nail coatings but also as paints and coatings for automobiles, commercial vehicles, trains, appliances, and metal structures such as steel fabrications. The monomeric components of coats not only are polymerized into long carbon chains by photolytic action but are also crosslinked with carbon chains between these chains through the use of di, tri and tetra (meth)acrylate oligomers. Strength of the crosslinked or photopolymerized compositions is also increased by use of urethane (carbamate) chains within the three dimensional structure of the polymerized composition. The result of extensive crosslinking of these compositions produces coatings that are impervious to all manner of attack including scratching, chipping, organic solvents, abrasives and ordinary environmental activity. These qualities are benefits for most fields because they provide permanent, impervious, non-removable, strong but flexible protective coatings for metals and other substrates that would otherwise be susceptible to environmental degradation.

Because these same coatings are used for nail coatings, these beneficial attributes for other commercial fields such as auto polymer coats become problematic for nail polymer coats. A nail polymer coat should be removable. However, a nail polymer coat that mimics the ingredients, concentrations and extent of crosslinking of auto polymer coats, would be highly undesirable. Once applied, it could not be removed from a nail. Growth of the nail would be the only practical but unsightly manner of removal of such a polymer coat.

To solve this problem, nail polymer coat manufacturers have lowered the degree of crosslinking, employed additional components to soften the photopolymerized or cured coating and incorporated solvent-soluble film formers to enable solvent removal. The patent literature describes attempts to provide a cured nail coat that is both tough, flexible, scratch and abrasion resistant yet can be easily removed by soaking the cured or photopolymerized coating in organic solvent. The literature describes nail polymer coatings composed of (meth)acrylate monomers, di and tri (meth)acrylate crosslinkers and preformed polymeric film formers that deliver tough, flexible cured nail coatings that can be removed by soaking with organic solvent.

These cured compositions are interpenetrating networks of mutually incompatible polymeric materials so that substantially homogeneous coatings are not produced. Instead, these coatings have a continuous phase of one polymeric material in which is dispersed a separate discontinuous phase of the second polymer. This construction enables some removability by organic solvents but also lessens the strength and toughness of the cured composition. Therefore, there is a need to develop nail polymer coatings that are both readily removable while demonstrating the strength and toughness of cured coatings such as those used in other commercial settings.

SUMMARY

The present invention is directed to a photopolymerizable nail coating, to the corresponding photopolymerized nail coating, a method of application and curing the photopolymerizable nail coating and a nail with a photopolymerized nail coating.

Compositional aspects of the photopolymerizable nail coating include (meth)acrylate monomers, di(meth)acrylate oligomers, and ethyl cellulose. The composition does not contain organic solvent or aqueous solvent, the di(meth) acrylate oligomers are a pair of moderately high weight average molecular weight oligomer and a very low weight average molecular weight oligomer. The monomers include at least a hydroxyl ester of (meth)acrylic acid, preferably a mixture thereof, and more preferably also includes isobornyl (meth)acrylate. The compositional aspects of the photopolymerizable coating also include a phosphine oxide photoinitiator and optional color components, optional surfactants, optional translucent microparticles as well as optional oxidation and spontaneous polymerization inhibitors.

The photopolymerizable nail coating is formulated as a single, substantially to essentially homogeneous mixture of the components of the composition constituting the photopolymerizable nail coating. It is stable and does not separate into individual components.

The photopolymerized nail coating is produced by exposure to UV also known as actinic radiation for a period of time sufficient to photopolymerize the monomeric components and at the same time to crosslink the oligomers with the monomeric components. The dual oligomer component enables short and long crosslinks which in part contribute to the physical macromolecular construct of the photopolymerized nail coating. The ethyl cellulose is miscible within the photopolymerized (meth)acrylate network. The combination is a substantial to essential uniform mixture of these two network components.

Application of the photopolymerizable nail coating is accomplished by brush, spray, drip or similar application technique. A portion of the photopolymerizable nail coating is applied to the nail or appropriate part of the nail. The photopolymerizable coating is exposed to UV radiation to cause curing. If designs are to be made, the first portion of photopolymerizable coating may constitute an outline or other appropriate configuration of the design. Following the cure of the first portion, subsequent portions of appropriate colored or clear photopolymerizable coatings are sequentially applied and cured to for the desired design. Application can be accomplished by artistic means such as would be applied by water color or oil base paint and easel.

The typical photopolymerized nail coat is a clear top coat usually applied over a color coat. According to the invention, aspects of the top coat and color coat involve the same compositional aspects. The top coat is clear while the color coat contains added color components.

DETAILED DESCRIPTION

The present invention is directed to a photopolymerizable nail coating that preferably is an at least substantially homogenous liquid composition that can be photopolymerized to produce an at least substantially homogeneous solid mixture or substantially homogeneous solid solution of polymerized (meth)acrylate components and ethyl cellulose. The photopolymerized nail coating is an interpenetrating network of the crosslinked (meth)acrylate components and ethyl cellulose. The interpenetrating network is phase miscible rather than phase separate.

Definitions

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The (meth)acrylate monomers are acrylate and methacrylate ester compounds wherein the esterifying alcohol is an aliphatic monoalcohol or an aliphatic diol. The aliphatic group preferably is an alkylene group of two to 10 carbons or is a branched or cyclic alkyl group of three to 10 carbons. The parenthesis surrounding the prefix "meth" means that the term (meth)acrylate encompasses methacrylic acid and acrylic acid compounds. Without a parenthesis, the term methacrylate means only the methacrylate esters, and does not include acrylic esters. The suffix "ate" means that the term (meth)acrylate is an ester formed by combination of a monoalcohol or diol with methacrylic acid or acrylic acid. Preferred (meth)acrylates include hydroxyethyl (meth)acrylate, hydroxypropyl (meth)acrylate and isobornyl (meth)acrylate and preferred (meth)acrylates are methacrylates.

The crosslinker di(meth)acrylates (also termed herein dicarbamates) are chain extended straight chain oligomers having (meth)acrylate moieties at both ends of the oligomer. The backbone of the oligomer between the two (meth)acrylate end groups may be any one of several backbones, including polyols such as polyethylene glycol, polypropylene glycol, polybutylene glycol, diurethane glycols formed by combination of a diol and a diisocyanate so as to form a central diol moiety coupled to a diisocyanate at each terminal hydroxyl of the diol and a diol coupled to the other terminus of the diisocyanate so as to form a diol-carbamate-diol-carbamate-diol moiety. The terminal hydroxyls of this backbone form the ester groups with the (meth)acrylate termini. The chain length of the diurethane glycol backbone can be extended or shortened by the number and length of the diols and diisocyanates used. Alternatively, the diisocyanate can be the central moiety each end of which is coupled to a hydroxyl of the diol and the other hydroxyl forms the ester moiety of the (meth)acrylate termini. Alternatively, polyol and diisocyanate roles of this backbone can be reversed so that the termini of the intermediate are isocyanate groups, e.g., an excess of diisocyanate is coupled with the polyol so that the backbone intermediate ends with the isocyanate moiety of the diisocyanate (the other end of the diisocyanate being combined with the hydroxyl of the polyol to form the carbamate group). In this backbone reversal, the isocyanate termini of the backbone intermediate are coupled with the hydroxyl of an hydroxyalkyl (meth)acrylate to form the oligomer. In addition and as a further alternative, the diisocyanate can be the central moiety, each end of which is coupled to an hydroxyl of the hydroxyalkyl (meth)acrylate moiety.

In the context of this invention, the terms di(meth)acrylate crosslinker and dicarbamate crosslinker are synonyms for the same crosslinker compound or compounds. Preferred crosslinker di(meth)acrylate oligomers are dimethacrylate oligomers.

The (meth)acrylate monomers are liquids and act as reactive solvents for the solid components of the photopolymerizable nail coating. Isobornyl (meth)acrylate in particular moderates the viscosity of the photopolymerizable coating so that as polymerization proceeds, the ability of the ethylenic groups such as the (meth)acrylate groups are able to engage in kinetic motion so as to facilitate ethylenic ((meth)acrylate) polymerization.

The molecular weight of a polymer or oligomer used according to the invention may be measured by a weight average molecular weight. The distribution of molecules of different molecular weights of a polymer or oligomer used according to the invention is determined by its polydispersity index. Molecular weight is expressed as Daltons (Da) and kiloDaltons (kDa). The acronym "wmw" stands for weight average molecular weight. Polydispersity is a unitless number and indicates the breadth of the Gaussian curve plotted as the molecular weight of individual molecules (X axis) against the number of molecules at each molecular weight (Y-axis).

The terms "photopolymerizable" and "photopolymerized" are understood to mean respectively a polymerizable mixture of ingredients and a polymerized material. Synonyms for photopolymerizable and photopolymerized are curable and cured or polymerizable and polymerized.

The terms "sol" and "gel" are understood to mean liquid and solid portions of a polymerizing composition. An unpolymerized mixture of monomers and a crosslinker is typically a low viscosity, fluid liquid. This is the sol stage of the mixture. As polymerization proceeds, the monomers polymerize to become long linear chains. If no crosslinker is present, the result of this polymerization is a thermoplastic polymer. If a crosslinker is present, it links the individual chains together to form a three dimensional net or network. With either of these polymerization processes, the growing polymer becomes solid. The solid fraction of the polymerizing composition is the gel stage. At the beginning of the polymerization, the sol is a continuous phase and the gel is miniscule and is a discontinuous phase. As polymerization proceeds, the concentration of sol lessens and the concentration of gel increases. The point of polymerization where the gel becomes the continuous phase and the sol is the discontinuous phase is the gelation point. With thermoplastic polymerization, the gel point occurs late in the polymerization. With thermoset polymerization where a moderate to high amount of crosslinker is present, the gel point occurs early in the polymerization. Typical gel points for thermoset polymers occur at a moderately retarded time when at least 3 to 5 weight percent of crosslinker is present and occur moderately early when at least 15 weight percent of crosslinker is present.

The term "about" is understood to mean ±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

The term "non-solvent" is understood to mean no organic liquid solvent such as ethyl acetate, methyl ethyl ketone, acetone, mono alcohols such as methanol, ethanol, propanol or butanol, or any other organic solvent having an STP boiling point of 100° C. or lower and in which (meth) acrylate monomers and oligomers and ethyl cellulose will dissolve.

The terms "non-hydrogen bonding" and its synonym "hydrophobic" are understood to mean a compound or group that does not contain a hydroxyl group and instead presents a non-polar aliphatic group. Compounds and groups that have carbonyls such as an ester, for example isobutyl (meth)acrylate, are non-hydrogen bonding or hydrophobic in this context.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

The Photopolymerizable Nail Coating

The photopolymerizable nail coating is formed with a composition of one or more (meth)acrylate monomers, ethyl cellulose and a combination of two (meth)acrylate crosslinkers. Additional components of the composition include a photoinitiator such as a phosphine oxide, as well as optional components such as an oxidation inhibitor, colorant, translucent microparticles, surfactant and stabilization agents. The photopolymerizable nail coating is a non-solvent, substantially homogeneous mixture of these components.

The pair of di(meth)acrylate crosslinkers includes a first one of moderately high weight average molecular weight and a moderately broad polydispersity, and a second one of moderately low weight average molecular weight and a moderately narrow polydispersity. The weight average molecular weight of the first crosslinker is in the range of 13 kDa to 17 kDa with a polydispersity of 1.5 to 2.5 while the weight average molecular weight of the second crosslinker is 500 Da to 700 Da with a polydispersity of 1.2 to 1.6. The preferred wmw of the first crosslinker is about 15 kDa with a polydispersity of about 1.5 to about 2.2. The preferred wmw of the second crosslinker is about 600 Da with a polydispersity of about 1.2 to about 1.4. The preferred di(meth)acrylate crosslinkers are dimethacrylate crosslinkers.

The crosslinker aspect of the invention encompasses any pair of di(meth)acrylate crosslinkers having the foregoing weight average and polydispersity characteristics and having either a polyol or a polyol-carbamate backbone. A preferred pair of crosslinkers includes those formed with a polyol, trimethylhexyl diisocyanate and methacrylic acid or hydroxyethyl methacrylate. The preferred polyol is ethylene glycol. The variation of weight average molecular weight for establishing the moderately high and moderately low weight average molecular weights of the two crosslinkers can be accomplished by increasing the length of the backbone. Formation of multiple backbone units of the combination of a multiple number (n) of trimethythexyl diisocyanates (Y groups) and multiple number+1 (n+1) of ethylene glycols (X group) enables this backbone variation. For example, combination of two Y groups and three X groups produces HO—X—Y—X—Y—X—OH as the hydroxyl terminated backbone. Variation can also be accomplished by use of a higher weight average molecular weight polyol, such as polyethylene glycol, for the middle X groups of the foregoing example and use of ethylene glycol for the terminal X groups. Capping the hydroxyl termini of the backbone with methacrylic acid forms the di(meth)acryl ale crosslinker 1.

Another version of the crosslinker having the foregoing weight average molecular weight and polydispersity parameters is crosslinker II which encompasses a backbone intermediate of one or more polyols (i.e. an m number of polyols) with m+1 diisocyanates (Y) so as to provide the backbone intermediate with isocyanate termini of the formula Y—$(X)_m$—$(Y—X)_l$—Y wherein l is zero or 1. This is the reverse of the backbone intermediate for crosslinker I. Extended crosslinker I backbone intermediate is terminated by hydroxyls while extended crosslinker II backbone intermediate is terminated by isocyanates. These isocyanate termini are combined with the hydroxyl of an hydroxyalkyl (meth)acrylate to form the chain extended crosslinker II of the formula (meth)acryloyl-O-alkylenyl-O—Y—$(X)_m$—$(Y—X)_1$—Y—O-alkylenyl-O-(meth)actyloyl wherein the alkylenyl group can be a multi-methylenyl group of 2 to 6 carbons, preferably 2 or 3 carbons, more preferably 2 carbons. The Y—O bonding group and the Y—X bonding group in this formula are the carbamate group —N—(=O)—O—.

Preferred polyols for the chain extended crosslinker I and chain extended crosslinker II are ethylene glycol and polyethylene glycol containing from 2 to 500 glycol units, preferably from 5 to 400 glycol units, more preferably from 10 to 250 glycol units, most preferably from 100 to 250 glycol units. The moderately high wmw cross linker includes a polyethylene glycol of a number of glycol units to provide the moderately high wmw. The moderately low wmw cross linker includes ethylene glycol or a polyethylene glycol of a number of glycol units to provide the moderately low wmw. The pair of moderately high and moderately low wmw crosslinkers is believed to facilitate effective crosslinking as the polymerizing composition reaches and passes the gel point. The moderately low wmw crosslinker helps promote molecular (kinetic) translation during the polymerization process and in particular when the viscosity and gel stage retard and/or tend to inhibit molecular movement or kinetic translation.

The monomer aspect of the invention encompasses (meth)acrylate ester monomers that display hydrogen bonding so as to facilitate non-covalent bonding with color coat and/or base coat nail coverings. The viscosity of the photopolymerizable nail coating is managed by incorporation of a (meth)acrylate ester that does not display hydrogen bonding. The ratio of hydrogen bonding to non-hydrogen bonding (meth)acrylate esters facilitates this factor. While it is not a parameter of the invention, it is believed that the inclusion of the non-hydrogen bonding (meth)acrylate facilitates retardation of viscosity elevation during the (meth)acrylate polymerization process. It is well known that a crosslinking polymerization process involves a sol stage at the outset of polymerization and a gel stage as polymerization and cross-linking proceed. The ultimate result of a highly crosslinked polymer is achievement of a gel stage in which a molecule of infinite molecular weight and size is produced. In other words, all monomers and crosslinkers in this ideal construction have been joined together as a single molecular network. This network is impervious to most exogenous agents and holds the monomeric units of the polymer in a substantially inflexible, non-translatable form. In practice, however, such a network composed of a single polymeric molecular of infinite size is not achieved because as polymerization proceeds, the translational motion of the unpolymerized monomers and oligomers becomes less. The lack of translational motion inhibits full and complete polymerization of all monomers and oligomers of the mixture into a single network. The lack of translational motion is due to the increase in viscosity of the polymerizing mixture. The typical result of this process is the production of a large number of polymer molecules of varying lengths as indicated by the weight average molecular weight and polydispersity.

Viscosity is not only affected by the polymerization process but also by hydrogen bonding of the (meth)acrylate ester monomers displaying hydrogen bonding properties. To ameliorate the elevation of viscosity during polymerization, a non-hydrogen bonding (meth)acrylate is incorporated into the composition constituting the photopolymerizable nail coating. These (meth)acrylate esters include butyl, pentyl, hexyl, heptyl and octyl (meth)acrylate as well as cyclohexyl (meth)acrylate and isobornyl (meth)acrylate, isobornyl (meth)acrylate is preferred not only because of its viscosity retardation effect but also because of its reactive solvation of the other components of the photopolymerizable nail coating. In part because of these properties of isobornyl (meth) acrylate, an organic solvent such as ethyl alcohol or ethyl acetate is not present in the photopolymerizable nail coating of the invention. In addition, the isobornyl (meth)acrylate retards the onset of the gel point during the polymerization process and retards the elevation of attendant viscosity during this process. This aspect is believed to facilitate incorporation of ethyl cellulose as a miscible component within the polymerizing (meth)acrylate network.

The (meth)acrylate esters displaying hydrogen bonding properties include hydroxyethyl (meth)acrylate, hydroxypropyl (meth)acrylate, hydroxybutyl (meth)acrylate and hydroxycyclohexyl (meth)acrylate. Preferred esters of this category include hydroxyethyl and hydroxypropyl (meth) acrylates. A more preferred ester of this category includes hydroxypropyl (meth)acrylate. In part because of their liquid character at ambient temperature, the hydrogen bonding (meth)acrylate esters contribute to the solubility aspect of the photopolymerizable nail coating so that an ordinary nonreactive organic solvent such as ethyl alcohol or ethyl acetate is not present.

Preferred (meth)acrylate monomers are methacrylate monomers.

Ethyl cellulose is a component of the compositional aspect of the photopolymerizable nail coating of the invention. Ethyl cellulose is fully miscible with the (meth)acrylate monomers and di(meth)acrylate crosslinker pair of this composition. Ethyl cellulose is also soluble in the polymerized network of the monomers and crosslinker pair so that the photopolymerized (cured) nail coating constitutes a substantially homogeneous polymeric network.

Ethyl cellulose is commercially available as different grades of ethoxylated hydroxyls of cellulose. The cellulose backbone also is available in different backbone lengths. For example, Dow describes its Ethocel® as having the structure wherein the numbers of anhydroglucose units and ethoxy groups determine the grade of Ethocel®:

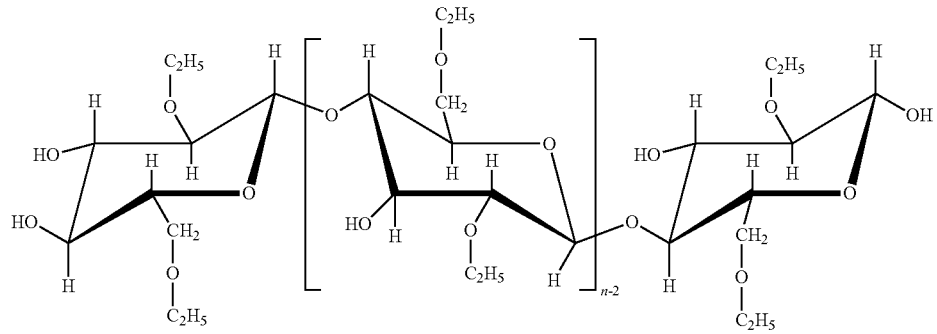

Structure of ETHOCEL™ Ethylcellulose

Ethyl cellulose is a film former product and is soluble in aliphatic alcohols, chlorinated solvents and natural oils but is insoluble in glycerin, propylene glycol and water according to Dow. This information indicates that ethyl cellulose should not be soluble in the highly polar compositional aspect of the photopolymerizable nail coating of the present invention. However, it has been discovered that by adjusting the concentration ratio of hydrogen bonding and non-hydrogen bonding monomers as well as the concentration of the di(meth)acrylate crosslinker pair, ethyl cellulose having an ethoxy content of 46 to 49 percent relative to the total number of hydroxyls of the cellulose backbone and a viscosity of about 3 to about 8, preferably about 3 to about 5.5 mPa's is substantially to fully miscible with the other components of the composition of the photopolymerizable nail coating. Moreover, these parameters of the ethyl cellulose render it miscible with the crosslinked polymer aspect of the photopolymerized nail coating.

The monomer concentrations of the compositional aspect of the photopolymerizable nail coating on a weight percentage basis relative to the total weight of the composition ranges from about 40 to about 60 weight percent (wt %), preferably 45 to 55 weight percent. The individual monomer concentrations relative to the total weight of the composition have the following ranges:

A) Hydrogen bonding (meth)acrylates—about 25 wt % to about 60 wt %, preferably about 30 wt % to about 40 wt %, more preferably about 33 wt % to about 38.5 wt %;

B) Non-hydrogen bonding (meth)acrylates—about 2 wt % to about 25 wt %, preferably about 2 wt % to about 12 wt %, more preferably about 2 wt % to about 5 wt %:

Preferred (meth)acrylate monomers and their concentrations include:

1) hydroxypropyl (meth)acrylate—about 25 wt % to about 60 wt %, preferably about 30 wt % to about 36 wt %, more preferably about 31 wt % to about 34 wt %:
2) hydroxyethyl (meth)acrylate—about 0 wt % to about 15 wt %, preferably about 2 wt % to about 5 wt %, more preferably about 2 wt % to about 4.6 wt %;
3) isobornyl (meth)acrylate about 0 wt % to about 25 wt %, more preferably about 2 wt % to about 25 wt %, most preferably about 2 wt % to about 15 wt %.
4) Preferred (meth)acrylate monomers are methacrylate monomers.

The concentrations of the crosslinker pair have the following weight percentage ranges relative to the total weight of the composition:

A) First crosslinker of moderately high wmw, from about 25 wt % to about 35 wt %, preferably about 27 wt % to about 33 wt %;

B) Second crosslinker of moderately low wmw, from about 10 wt % to about 20 wt %, preferably about 12 wt % to about 18 wt %, more preferably about 14 wt % to about 16 wt %.

The concentration of ethyl cellulose in weight percentage relative to the total weight of the composition is from about 2 to about 4 wt %, preferably about 3 wt %.

Any suitable photoinitiator or combination may be combined with the other components of the photopolymerizable nail coating to enable photopolymerization. Phosphine oxide photoinitators can be employed alone or in combination with benzophenone derivatives as well as with benzyl ketals, alpha hydroxyl alkyl phenones and acetophenone derivatives. The phosphine oxides are commercially available and described in the literature. See U.S. Pat. Nos. 4,298,738; 4,737,592 and 6,298,738 and Irgacure® and Lucirin® brands of phenones and phosphine oxides. A particular phosphine oxide photoinitiator useful for inclusion in the photopolymerizable nail coating is ethyl-2,4,6-trimethyl-benzoyldiphenylphosphinate. Another is 2,4,6-trimethyl-benzoyldiphenylphosphine oxide. Another is hydroxycyclohexyl phenyl ketone, as well as benzyl dimethyl ketal. A typical concentration of the photoinitiator may range from 0.1 wt % to 20 wt %, preferably about 0.1 wt % to about 10 wt %, more preferably about 0.2 wt % to about 5 wt % relative to the total weight of the composition.

Inclusion of one or more polymerization regulators and anti-oxidation agents may also be desirable. These include hydroquinones and ascorbic acid derivatives. These regulators and agents may range in concentration from 0.0001 wt % to about 5 wt %.

Inorganic pigments and dyes such as ferric oxide; FD&C red 4, 6, 7, 17, 21, 22, 27, 28 or 33; FD&C yellow 5 or 6; D&C violet 2, 3 or 4; titanium oxide; D&C orange 4, 5 or 10; FD&C green 3, 5 or 6, and similar colorants may be employed. Suitable concentrations range from 0.01 wt % to 0.05 wt %.

Surfactants, plasticizers and emulsifiers such as phthalates, camphor, castor oil, citrate esters, glyceryl diesters, glycolates and tartrates may be included as appropriate. Typical concentrations of about 0.2 wt % to about 1.0 wt % may be employed.

While it is not a limitation of the invention, it is believed that the photopolymerized nail coating of crosslinked poly ((meth)acrylate monomer(s) and the pair of di(meth)acrylate oligomers) and ethyl cellulose is a substantially homogeneous mixture rather than separate phases of (meth)acrylate polymer and ethyl cellulose. In particular, it is believed that the two polymer networks of the photopolymerized nail coating, which are the crosslinked (meth)acrylate polymer and the ethyl cellulose, constitute a mutually miscible interpenetrating network so that the polymer and the ethyl cellulose together form one solid phase rather than separate domains of polymer and ethyl cellulose. It is believed that this interaction contributes to the strength, toughness and flexibility of the photopolymerized nail coating. Nevertheless, in contrast to single phase crosslinked polymer coatings of nails, the photopolymerized nail coating according to the invention is readily removable by soaking with organic solvent such as ethyl acetate, methyl ethyl ketone and/or ethyl alcohol or mixtures thereof. In particular, the photopolymerized nail coating can be removed within 10 to 30 minutes of soaking, preferably 5 to 20 minutes. The soaking causes the coating to swell uniformly and loosen from the underlying surface which enables facile peeling of the coating as a single layer or as a few large pieces. This removal process preferably does not leave small to miniscule particles of cured coating which would need to be removed by sanding or filing. It is believed that the swelling phenomenon is due to the intimate, substantially homogeneous mixture of crosslinked (meth)acrylate polymer and ethyl cellulose. The ethyl cellulose enables solvent access into and throughout the photopolymerized coating. The substantially homogeneous character of the photopolymerized coating enables solvent access to all parts of the coating and causes uniform and complete swelling.

The photopolymerizable nail coating of the invention may be applied as a clear top coat to a bare nail or to a nail pre-coated with a base coat or with a base coat and color coat. The photopolymerizable nail coating of the invention may be combined with colorants and suspending agents such as plasticizers and emulsifiers to form a color coat.

Application of the photopolymerizable nail coating of the invention is accomplished by ordinary salon techniques. Use of fine brushes, fine spray pencils and sponge wipers are typical applicators useful for applying the photopolymerizable nail coating to nails and coated nails. Exposure to UV radiation produced with a UV light source will initiate polymerization. While dual UV wavelengths of the 405 and 365-385 nm ranges can be employed to photopolymerized the photopolymerizable nail coating, the longer waver length of 405 can be employed alone for this purpose. Other (meth)acrylate/film former nail coating compositions described in the art require the more energetic UV wavelength of 365-385 along with the longer UV wavelength. Without the boost in energy provided by this dual use, the resulting coating is dull, lacks luster and gloss. With the present photopolymerizable nail coating, however, the longer wave length UV irradiation is sufficient to produce a cured (photopolymerized) coating that displays luster and gloss and is not dull in appearance. This factor enables use of safer, less expensive equipment and avoids exposure of the hands of the person to possibly harmful high energy UV irradiation. The times for exposure may range from 10 seconds to 10 minutes, preferably 1 minute to 6 minutes.

Multiple applications of the photopolymerizable nail coating may also be employed especially if multicolor partial layers and/or designs are to be produced. Fine tip brush work similar to an artist painting with brush and easel can be employed for this purpose. Following each partial application, the applied coating can be exposed to UV radiation. However, the photopolymerizable nail coating used for such designs can be prepared to present a higher thixotropic property than is present in a single coating for the entire nail. In this manner, a single UV radiation can be applied following completion of the design and the design can be altered.

EXAMPLES

Example 1-Formulation Compositions (Amounts in Weight Percents (wt %))

| Composition/Formulation | New top coat: A | New top coat: B | New top coat: C |
| --- | --- | --- | --- |
| Di-HEMA Trimethylhexyl Dicarbamate (MW 15,000) | 27.6-32.2 | 27.6-32.2 | 27.6-32.2 |
| HEMA | 2.3-4.6 | 2.3-4.6 | 2.3-4.6 |
| IBOMA | 2.3-4.6 | 2.3-4.6 | 2.3-4.6 |
| Acrylic acid | 0.0-0.5 | 0.0-0.5 | 0.0-0.5 |
| Hydroxycyclohexyl Phenyl Ketone | 0.0-0.5 | 0.0-0.5 | 0.0-0.5 |
| D&C violet #2 | 0.0-0.5 | 0.0-0.5 | 0.0-0.5 |
| HPMA | 31.3-33.6 | 33.3-35.6 | 29.3-31.6 |
| Di-HEMA Trimethylhexyl Dicarbamate (MW 600) | 14.0 | 16.0 | 18.0 |
| Ethocel 4 | 3.0 | 3.0 | 3.0 |
| TPO | 5.0 | 5.0 | 5.0 |
| BDK | 1.0 | 1.0 | 1.0 |
| Total | 100.0 | 100.0 | 100.0 |

Example 2—Effect of Di-HEMA Trimethylhexyl Dicarbamate (MW 600) On Gloss and Abrasion Resistance a. General BYK opacity charts, BYK 76 μm drawdown bar, OPI LED GL900 Studio Light, OPI Expert Touch nail wipes, Kimberly-Clark cleaning wipes, DeFelsko thickness gauge, Horiba 1G-320 gloss meter, 3M 5000 grit sandpaper, SDL Atlas crockmeter were used.

b. Formulations

OPI Gel Top coat GC030, the commercially available gel coating formulation was used as the standard reference. The standard reference was compared with Top coat formulas A, B and C of Example 1.

c. Method

Drawdowns of formulations A, B and C were applied on opacity charts using the 76 μm drawdown bar and cured under the LED Studio light, with a 405 nm wavelength radiation and a power of 32 watts, for 30 seconds. The tacky layer was removed using a nail wipe soaked in isopropanol. Initial gloss was measured using the gloss meter at a 60° angle. Initial film thickness was measured using the coating thickness gauge.

The opacity chart with the drawdown was then placed on a crockmeter. A fresh piece of 5000 grit sandpaper was used as abrasion media and attached to the 2 pound weighted rubbing arm. The drawdown surface was abraded using 50 consecutive rubbing cycles. The drawdown was cleaned using a dry wipe. Gloss and thickness after abrasion were measured as described above. Gloss drop was calculated as a percentage of initial gloss and thickness loss as the difference between initial and final thickness.

d. Results

| Formulation | Standard Reference | New top coat: A | New top coat: B | New top coat: C |
| --- | --- | --- | --- | --- |
| Initial gloss (GU) | 85.6 ± 0.6 | 85.5 ± 0.2 | 82.5 ± 0.9 | 85.4 ± 1.1 |
| Gloss drop (%) | 28 | 18 | 16 | 29 |
| Thickness loss (μm) | 1.93 ± 0.08 | 4.33 ± 0.30 | 2.67 ± 0.03 | 2.66 ± 0.01 |

Top coat formulations containing Di-HEMA Trimethylhexyl Dicarbamate (MW 600) had an initial gloss comparable to the standard reference formulation, as opposed to formulations without Di-HEMA Trimethylhexyl Dicarbamate (MW 600). Formulations containing Di-HEMA Trimethylhexyl Dicarbamate (MW 600) cured under a 405 nm radiation, while similar formulations available on the market containing non-reactive solvent-soluble polymers needed a 385 nm radiation in addition to the 405 nm radiation in order to obtain a good surface cure resulting in a high initial gloss.

The lowest gloss drop, which is equivalent to the best gloss retention, was obtained for formulations A and B. The thickness loss, which is equivalent to the best abrasion resistance, was similar for A, B and C, although it started to increase with decreasing Di-HEMA Trimethylhexyl Dicarbamate (MW 600) content in formulation A.

These results define a HEMA Trimethylhexyl Dicarbamate (MW 600) range between 14% and 16% required to obtain the optimal gloss and abrasion resistance to achieve top coat performance.

Example 3—Effect of Di-HEMA Trimethylhexyl Dicarbamate (MW 600) on Removal Time a. General McMaster-Carr drawdown glass plate size 30.5×20.3 cm, Graham Field Health Products Microscope glass slide size 25.4×76.2 mm, thickness 1-1.2 mm, BYK 4-sided bar, OPI LED GL900 Studio Light, OPI Expert Touch nail wipes were used.

b. Formulations

Base coat formulation: OPI Gel Base coat GC010 was used. Top coal formulations: OPI Gel Top coat GC030, Top coat formula A, B and C were used.

c. Method

The standard base coat was applied on a drawdown glass plate using the 4-sided bar with the 50 μm side. The base coat was exposed to the LED Studio light for 30 seconds. The top coat was then applied on top of the standard base coat using the 4-sided bar with the 100 μm side. The top coat was exposed to the LED Studio light for 30 seconds. The coating area was left under the turned-off light for 3 minutes. The first saturated nail wipe square was placed on the cured coatings 1 cm from the top of the coating area. A microscope glass slide was placed on top of the nail wipe square and the first timer was started. The second saturated nail wipe square was placed on the cured film 1 cm from the bottom of the coating area. A microscope glass slide was placed on top of the second nail wipe square and the second timer was started. The times when the nail wipe squares popped up from the glass slide were recorded and averaged for each test. The test was run 3 times for each top coat.

d. Results

| Formulation | Standard Reference | New top coat: A | New top coat: B | New top coat: C |
| --- | --- | --- | --- | --- |
| Removal time (seconds) | 78 ± 5 | 61 ± 4 | 62 ± 4 | 100 ± 9 |

Formulations A and B showed faster removal compared to the standard reference, respectively 22% and 20% shorter. Formulation C had a 28% longer removal compared to the standard reference. These results showed 16% is the upper limit for the Di-HEMA Trimethylhexyl Dicarbamate (MW 600) content in order to achieve faster removal compared to the standard reference.

Statements of Embodiments of the Invention

The following statements of embodiments of the invention (Statements 1-44) provide descriptions of the composition for forming a polymerized top coat, the photopolymerized composition, the photopolymerized top coat preferably on a base coating of a nail plate, a method for forming and a method for removing.

1. A composition suitable for formation of a polymerized coating on a nail, comprising: a non-solvent mixture of one or more (meth)acrylate monomers, ethyl cellulose and a combination of two di-(hydroxyethylmethacryloyl) trimethylhexyl dicarbamates, the first di carbamate having a weight average molecular weight in the range of 13 kDa to 17 kDa and the second dicarbamate having a weight average molecular weight in the range of 500 Da to 700 Da.
2. A composition according to statement 1 wherein the one or more (meth)acrylate monomers are at least hydroxypropyl (meth)acrylate.
3. A composition according to statement 1 wherein the one or more (meth)acrylate monomers are at least hydroxypropyl (meth)acrylate and hydroxyethyl (meth)acrylate.
4. A composition according to statement I wherein the one or more (meth)acrylate monomers consist essentially of hydroxypropyl (meth)acrylate, hydroxyethyl (meth)acrylate, isobornyl (meth)acrylate and acrylic acid.
5. A composition according to statement 1 wherein the one or more (meth)acrylate monomers consist essentially of hydroxypropyl (meth)acrylate.
6. A composition according to statement I wherein the weight percentage ranges of ingredients relative to the total weight of the composition are about 40 wt % to about 60 wt % for the (meth)acrylate monomers, about 2 wt % to about 4 wt % for the ethyl cellulose, about 25 wt % to about 35 wt % for the first dicarbamate and about 10 wt % to about 20 wt % for the second dicarbamate.
7. A composition according to statement 3 or statement 4 wherein the weight percentage ranges relative to the total weight of the composition are about 25 wt % to about 60 wt % for hydroxypropyl (meth)acrylate; about 0 wt % to about 15 wt % for hydroxyethyl (meth)acrylate, about 0 wt % to about 25 wt % for isobornyl (meth)acrylate and about 0 wt % to about 2 wt % for acrylic acid.
8. A composition according to any one of statements 1 to 7 wherein the composition is a substantially homogeneous mixture.
9. A composition according to one of statements 1 to 8 further comprising a phosphine oxide photoinitiator and the composition is capable of curing photolytically to a substantially homogeneous solid mixture.
10. A composition according to statement 9 wherein the solid mixture is a substantially homogeneous solid solution.
11. A composition according to statement 9 where in the solid mixture is a substantially homogeneous interpenetrating network.
12. A photopolymerized composition of a non-solvent mixture of one or more (meth)acrylate monomers, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700 Da.
13. A photopolymerized composition of statement 12 wherein the one or more (meth)acrylate monomers and two dicarbamates form a crosslinked poly(meth)acrylate network.
14. A photopolymerized composition according to statement 13 wherein the (meth)acrylate monomers include at least hydroxyethyl (meth)acrylate.
15. A photopolymerized composition according to statement 13 wherein the (meth)acrylate monomers include at least hydroxyethyl (meth)acrylate and hydroxypropyl (meth)acrylate.
16. A photopolymerized composition according to statement 13 wherein the (meth)acrylate monomers consist essentially of hydroxyethyl (meth)acrylate, hydroxypropyl (meth)acrylate, isobornyl (meth)acrylate and acrylic acid.
17. A photopolymerized composition according to statement 13 wherein the (meth)acrylate monomers consist essentially of hydroxylpropyl (meth)acrylate.
18. A photopolymerized composition of any one of statement 13 to 17 wherein the crosslinked poly(meth)acrylate network and the ethyl cellulose are a substantially homogeneous mixture of polymers.
19. A photopolymerized composition of statement 18 wherein the substantially homogeneous mixture is a substantially homogeneous solid solution.
20. A photopolymerized composition of statement 18 wherein the substantially homogeneous mixture is a substantially homogeneous interpenetrating network of the polymers.
21. A polymerized coating suitable for covering a nail comprising a photopolymerized composition of a non-solvent mixture comprising hydroxypropyl (meth)acrylate, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700 Da.
22. A polymerized coating according to statement 21 comprising a photopolymerized composition wherein the mixture further comprises hydroxyethyl (meth)acrylate.
23. A polymerized coating according to statement 22 comprising a photopolymerized composition wherein the mixture further comprises acrylic acid and isobornyl (meth)acrylate.

24. A polymerized coating according to any one of statements 21 to 23 wherein the polymerized coating is a substantially homogeneous mixture.
25. A polymerized coating according to statement 23 wherein the mixture is a substantially homogeneous solid solution.
26. A polymerized coating according to statement 23 wherein the mixture is a substantially homogeneous interpenetrating network.
27. A method for forming a polymerized coating on a nail comprising the steps of:
    coating a nail with a photopolymerizable composition of a non-solvent mixture of one or more (meth)acrylate monomers, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700, and
    exposing the photopolymerizable composition with UV radiation for a sufficient time to cure the composition and produce a polymerized coating.
28. A method according to statement 27 wherein the (meth)acrylate monomers comprise hydroxyethyl (meth)acrylate, hydroxypropyl (meth)acrylate, isobornyl (meth)acrylate and acrylic acid.
29. A method according to statement 27 wherein the (meth)acrylate monomers comprise hydroxypropyl (meth)acrylate.
30. A method according to statement 27 wherein the (meth)acrylate monomers comprise hydroxyethyl (meth)acrylate, hydroxypropyl (meth)acrylate and isobornyl (meth)acrylate.
31. A method according to any one of statements 27-29 wherein the polymerized coating is a substantially homogeneous mixture 32. A method according to statement 31 wherein the mixture is a substantially homogeneous solid solution.
33. A method according to statement 31 wherein the mixture is a substantially homogeneous interpenetrating network.
34. A method for removal of a polymerized coating of a photopolymerized composition of a non-solvent mixture of one or more (meth)acrylate monomers, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700, comprising: soaking the polymerized coating in an organic solvent to swell the polymerized coating.
35. A method of removal according to statement 34 wherein the organic solvent is acetone, methyl ethyl ketone, isopropanol, ethanol, methyl propyl ketone or any mixture thereof.
36. A method of removal according to statement 34 wherein the polymerized coating swells and peels in no more than 30 minutes.
37. A method of removal according to statement 34 wherein the polymerized coating completely peels in one or a few pieces and leaves essentially no residual particles.
38. A composition according to any one of statements 1 to 11 wherein the weight average molecular weight of the first dicarbamate is about 15 kDa and the weight average molecular weight of the second di carbamate is about 600 Da.
39. A photopolymerized composition according to any one of statements 12-20 wherein the weight average molecular weight of the first dicarbamate is about 15 kDa and the weight average molecular weight of the second dicarbamate is about 600 Da.
40. A polymerized coating according to any one of statements 21 to 26 wherein the weight average molecular weight of the first dicarbamate is about 15 kDa and the weight average molecular weight of the second dicarbamate is about 600 Da.
41. A method according to any one of statements 27 to 38 wherein the weight average molecular weight of the first dicarbamate is about 15 kDa and the weight average molecular weight of the second di carbamate is about 600 Da.
42. A composition according to statement 6 wherein the weight percent range of the first dicarbamate is about 27 wt % to about 33 wt % and the weight percent range of the second dicarbamate is about 14 wt % to about 18 wt %.
43. A composition according to statement 43 wherein the weight percent range of the first dicarbamate is about 27.6 wt % to about 32.2 wt % and the weight percent range of the second dicarbamate is about 16 wt %.
44. A composition, coating or method according to any one of statements 1-43 wherein the (meth)acrylate monomer or monomers and di(meth)acrylate crosslinker are methacrylate monomer or monomers and dimethacrylate crosslinker.

SUMMARY STATEMENTS

The inventions, examples and results described and claimed herein have may attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being methyl and ethyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

While the invention has been described in conjunction with the detailed description thereof, the foregoing description is intended to illustrate and not limit the scope of the invention, which is defined by the scope of the appended claims. Thus, from the foregoing, it will be appreciated that, although specific non-limiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A composition suitable for formation of a polymerized coating on a nail, comprising: a non-solvent mixture of one or more (meth)acrylate monomers, ethyl cellulose and a combination of two di-(hydroxyethylmethacryloyl) trimethylhexyl dicarbamates, the first dicarbamate having a weight average molecular weight in the range of 13 kDa to 17 kDa and the second dicarbamate having a weight average molecular weight in the range of 500 Da to 700 Da.

2. A composition according to claim 1 wherein the one or more (meth)acrylate monomers are at least hydroxypropyl (meth)acrylate.

3. A composition according to claim 1 wherein the one or more (meth)acrylate monomers are at least hydroxypropyl (meth)acrylate and hydroxyethyl (meth)acrylate.

4. A composition according to claim 1 wherein the one or more (meth)acrylate monomers consist essentially of hydroxypropyl (meth)acrylate, hydroxyethyl (meth)acrylate, isobornyl (meth)acrylate and acrylic acid.

5. A composition according to claim 1 wherein the one or more (meth)acrylate monomers consist essentially of hydroxypropyl (meth)acrylate.

6. A composition according to claim 1 wherein the weight percentage ranges of ingredients relative to the total weight of the composition are about 40 wt % to about 60 wt % for the (meth)acrylate monomers, about 2 wt % to about 4 wt % for the ethyl cellulose, about 25 wt % to about 35 wt % for the first dicarbamate and about 10 wt % to about 20 wt % for the second dicarbamate.

7. A composition according to claim 4 wherein the weight percentage ranges relative to the total weight of the composition are about 25 wt % to about 60 wt % for hydroxypropyl (meth)acrylate; about 0 wt % to about 15 wt % for hydroxyethyl (meth)acrylate, about 0 wt % to about 25 wt % for isobornyl (meth)acrylate and about 0 wt % to about 2 wt % for acrylic acid.

8. A photopolymerized composition of a non-solvent mixture of one or more (meth)acrylate monomers, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700 Da.

9. A photopolymerized composition of claim 8 wherein the one or more (meth)acrylate monomers and two dicarbamates form a crosslinked poly(meth)acrylate network.

10. A photopolymerized composition according to claim 9 wherein the (meth)acrylate monomers include at least hydroxyethyl (meth)acrylate.

11. A photopolymerized composition according to claim 9 wherein the (meth)acrylate monomers include at least hydroxyethyl (meth)acrylate and hydroxypropyl (meth)acrylate.

12. A photopolymerized composition according to claim 9 wherein the (meth)acrylate monomers consist essentially of hydroxyethyl (meth)acrylate, hydroxypropyl (meth)acrylate, isobornyl (meth)acrylate and acrylic acid.

13. A polymerized coating suitable for covering a nail comprising a photopolymerized composition of a non-solvent mixture comprising hydroxypropyl (meth)acrylate, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700 Da.

14. A polymerized coating according to claim 13 comprising a photopolymerized composition wherein the mixture further comprises hydroxyethyl (meth)acrylate.

15. A polymerized coating according to claim 13 comprising a photopolymerized composition wherein the mixture further comprises acrylic acid and isobornyl (meth)acrylate.

16. A method for forming a polymerized coating on a nail comprising the steps of:
    coating a nail with a photopolymerizable composition of a non-solvent mixture of one or more (meth)acrylate monomers, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700, and
    exposing the photopolymerizable composition with UV radiation for a sufficient time to cure the composition and produce a polymerized coating.

17. A method for removal of a polymerized coating of a photopolymerized composition of a non-solvent mixture of one or more (meth)acrylate monomers, ethyl cellulose, a phosphine oxide photoinitiator, and a combination of two dihydroxyethyl methacryloyl trimethylhexyl dicarbamates, the first dicarbamate having a weight average molecular weight in the range of 13 kDa to 17 kDa and the second dicarbamate having a weight average molecular weight in the range of 500 Da to 700, comprising: soaking the polymerized coating in an organic solvent to swell the polymerized coating.

18. A method of removal according to claim 17 wherein the polymerized coating completely peels in one or a few pieces and leaves essentially no residual particles.

19. A composition according to claim 1 wherein the weight average molecular weight of the first dicarbamate is about 15 kDa and the weight average molecular weight of the second dicarbamate is about 600 Da.

20. A composition according to claim 1 wherein the (meth)acrylate monomer or monomers and di(meth)acrylate crosslinker are methacrylate monomer or monomers and dimethacrylate crosslinker.

* * * * *